US010650316B2

(12) United States Patent
Huang et al.

(10) Patent No.: US 10,650,316 B2
(45) Date of Patent: May 12, 2020

(54) ISSUE-MANAGE-STYLE INTERNET PUBLIC OPINION INFORMATION EVALUATION MANAGEMENT SYSTEM AND METHOD THEREOF

(71) Applicant: Chunghwa Telecom Co., Ltd., Taoyuan County (TW)

(72) Inventors: Hua-Tai Huang, Taoyuan County (TW); Meng-Hsin Yang, Taoyuan County (TW); Po-Wei Huang, Taoyuan County (TW)

(73) Assignee: Chunghwa Telecom Co., Ltd., Taoyuan County (TW)

( * ) Notice: Subject to any disclaimer, the term of this patent is extended or adjusted under 35 U.S.C. 154(b) by 903 days.

(21) Appl. No.: 14/614,167

(22) Filed: Feb. 4, 2015

(65) Prior Publication Data

US 2016/0098738 A1 Apr. 7, 2016

(30) Foreign Application Priority Data

Oct. 6, 2014 (TW) .............................. 103134690 A

(51) Int. Cl.
*G06N 7/00* (2006.01)
*G06Q 30/02* (2012.01)
(Continued)

(52) U.S. Cl.
CPC ............. *G06N 7/005* (2013.01); *A61B 5/163* (2017.08); *A61B 5/165* (2013.01); *G06F 16/93* (2019.01);
(Continued)

(58) Field of Classification Search
None
See application file for complete search history.

(56) References Cited

U.S. PATENT DOCUMENTS 8,117,227 B2 * 2/2012 Montangero .......... G06Q 30/02
707/709
9,916,538 B2 * 3/2018 Zadeh .................... G06K 9/627
(Continued)

FOREIGN PATENT DOCUMENTS

| CN | 102855276 | 1/2013 |
| CN | 103365902 | 10/2013 |
| CN | 103577404 | 2/2014 |

*Primary Examiner* — Gurkanwaljit Singh
(74) *Attorney, Agent, or Firm* — Amin, Turocy & Watson, LLP

(57) ABSTRACT

The present invention is related to an issue-manage-style internet public opinion information evaluation management system and method thereof. The system mainly comprises 5 modules of 1) Issue establish/setup module for establishing new issue and the keywords thereof; 2) public opinion information collection module for retrieving and analyzing data retrieved by dredge technology, program, and community web-site open API; 3) public opinion information reputation analysis module for calculating each public opinion information evaluation score by text reputation analysis and community interactive fuzzy analysis; 4) issue trend analysis module for calculating issue trend score by disclosed method based on daily, weekly, or monthly public opinion information reputation evaluation score; 5) issue related public opinion information exchange module for presenting issue related public opinion information on each management interface or message alert of each system via internet exchange standards.

6 Claims, 3 Drawing Sheets

(51) Int. Cl.
    *A61B 5/16*       (2006.01)
    *G06K 9/62*       (2006.01)
    *G06F 40/30*      (2020.01)
    *G06Q 50/00*      (2012.01)
    *G06F 16/93*      (2019.01)

(52) U.S. Cl.
    CPC ............ *G06F 40/30* (2020.01); *G06K 9/627* (2013.01); *G06Q 30/0201* (2013.01); *G06Q 30/0203* (2013.01); *G06Q 50/01* (2013.01)

(56) References Cited

U.S. PATENT DOCUMENTS

| | | | |
|---|---|---|---|
| 2008/0120129 A1* | 5/2008 | Seubert | G06Q 10/06 705/35 |
| 2011/0078157 A1 | 3/2011 | Sun et al. | |
| 2012/0221485 A1* | 8/2012 | Leidner | G06Q 10/0635 705/36 R |
| 2012/0296845 A1* | 11/2012 | Andrews | G06Q 40/06 705/36 R |
| 2013/0311485 A1 | 11/2013 | Khan | |
| 2014/0201126 A1* | 7/2014 | Zadeh | G06K 9/627 706/52 |

\* cited by examiner

ISSUE-MANAGE-STYLE INTERNET PUBLIC OPINION INFORMATION EVALUATION MANAGEMENT SYSTEM AND METHOD THEREOF

BACKGROUND OF THE INVENTION

1. Field of the Invention

The present invention is related to an issue-manage-style internet public opinion information evaluation management system and method thereof. More particularly, the present invention is related to data management and exchange system among an internet information group with evaluated issue relevance.

2. Description of the Prior Art

The fast growing of community web-site service, dynamics of community web-site issues rapidly influence management of a company even an individual business. Thus, monitoring and/or managing public opinion information and/or issue evaluation have become very important recently. Internet community builds up its reputation based on customer's real experience and sharing. These reviews or opinions exist in many internet forums, blogs, and community web-sites, which is oriented to particular issues and the evaluations grows rapidly. It greatly influences products, services, and brand value of a company. In the past, users face five major problems of hard to collect public opinion information, orderless and/or overloading information of collected public opinion information, human-power oriented information analysis, hard to observe potential issue among huge public opinion information, and hard to track issue.

Taiwan published patent application no. TW201137632 disclosed technologies of a system and method thereof of document feeling analysis based on document and calculation of space vector and feeling vector among readers and the writer corresponding to different linked feelings of a document. The documents are divided into different level of feeling by different colors in the system and method thereof.

China patent no. 102073646A disclosed technologies focusing on analysis of words/sentences of text. It calculates trend of each word/sentence toward a topic, including positive trend and negative trend, and the calculation would indicate a topic with most trends as the case need to be watched.

SUMMARY OF THE INVENTION

Regarding to the aforementioned problems of conventional technologies, the objective of the present invention is to provide an issue-manage-style internet public opinion information evaluation management system and method thereof. It is able to collect and structure news, blog, social web-site, forum, reviews of Apps, and etc. It is able to combine text reputation analysis and community mutual-action analysis to fast establish reputation evaluation in response to internet public opinion information and issue. Also, based on issue management, it is able to continuously observe the development of a particular issue and trend thereof at different times by issue management. It is also easy to monitor public opinion information, manage community, and integrate related system by sharing information which meets certain international standards.

The issue-manage-style internet public opinion information evaluation management system of the present invention comprises of an issue establish/manage module, a public opinion information collection module, a public opinion information reputation evaluation module, an issue trend analysis module, and an issue related public opinion information data exchange module. The issue establishment/management module is configured to establish a plurality of issues and keywords, generate a setup configuration, and manage the issues, and the issues correspond to the keywords. The public opinion information collection module is configured to collect data from a plurality of heterogeneous data sources and transfer the data into a structured data format. The public opinion information reputation evaluation module is configured to calculate a public opinion information positive/negative evaluation. The issue trend analysis module is configured to calculate an issue positive/negative evaluation. The issue related public opinion information data exchange module is configured to be connected to the aforementioned modules to enable the modules access to the public opinion information positive/negative evaluation and the issue positive/negative evaluation.

The steps to the issue-manage-style internet public opinion information evaluation management method of the present invention comprises of: analyzing an article by a reputation dual-index positive/negative evaluation analysis method to retrieve a first reputation index and a second reputation index; generating a public opinion information evaluation score according to the first reputation index and the second reputation index; and adjusting the public opinion information evaluation score by an issue evaluation analysis method and retrieving an issue reputation score mainly related to the issue.

The issue-manage-style internet public opinion information evaluation management system and method thereof have one or more advantages as below:

1. The system is based on issue and data characters requested by the issue, which is able to collect assigned web-site information from dredge-denied web-site and dredge web-site, wherein dredge technologies mean that the system analyzes contents and characters of a web-site then establishes content indexes for searching, wherein the collected information is structured information instead of RAW DATA, which is defined by data requested by the issue. Dredge-denied web-sites comprise social web-site, application software market of smart phone, blog community and forum, and dredge-allowable web-sites comprise internet news media.
2. The information collected for issue would be analyzed by public opinion reputation information analysis and derived a plurality of quantized evaluation information, wherein the evaluation scores can be retrieved by combination of natural semantic analysis technologies and community fuzzy technologies. The information with public opinion evaluation score can be treated as public opinion information, and each assigned issue can get corresponding public opinion information by keywords and evaluation score, meanwhile, by the mechanism, the issue can automatically track development of public opinion information for automatically and fast knowing the public opinion information.
3. Each issue, based on each public opinion information evaluation score, would decrease its influence as time goes by, thus the public opinion information corresponding to each issue would be considered with its time influence for calculating and getting a today's issue positive evaluation score, positive public opinion information representing group, negative evaluation score, negative public opinion information representing group, and the same method can be adopted for calculating weekly evaluation or monthly evaluation of the issue for fast monitoring trend variation of the issue.

4. The system is designed based on issue to execute internet public opinion information evaluation management, which is able to extend to dredge-denied internet information to complete public opinion information collection, and is able to automatically analyze public opinion information and issue evaluation, thus the user is able to easily focus on, track, and get evaluation. The present invention can reduce cost of internet information collection/analysis, and can be applied in positive evaluation improvement and negative evaluation cancellation of brand, product, service, and marketing.

DETAILED DESCRIPTION OF THE PREFERRED EMBODIMENT

Figure 1:
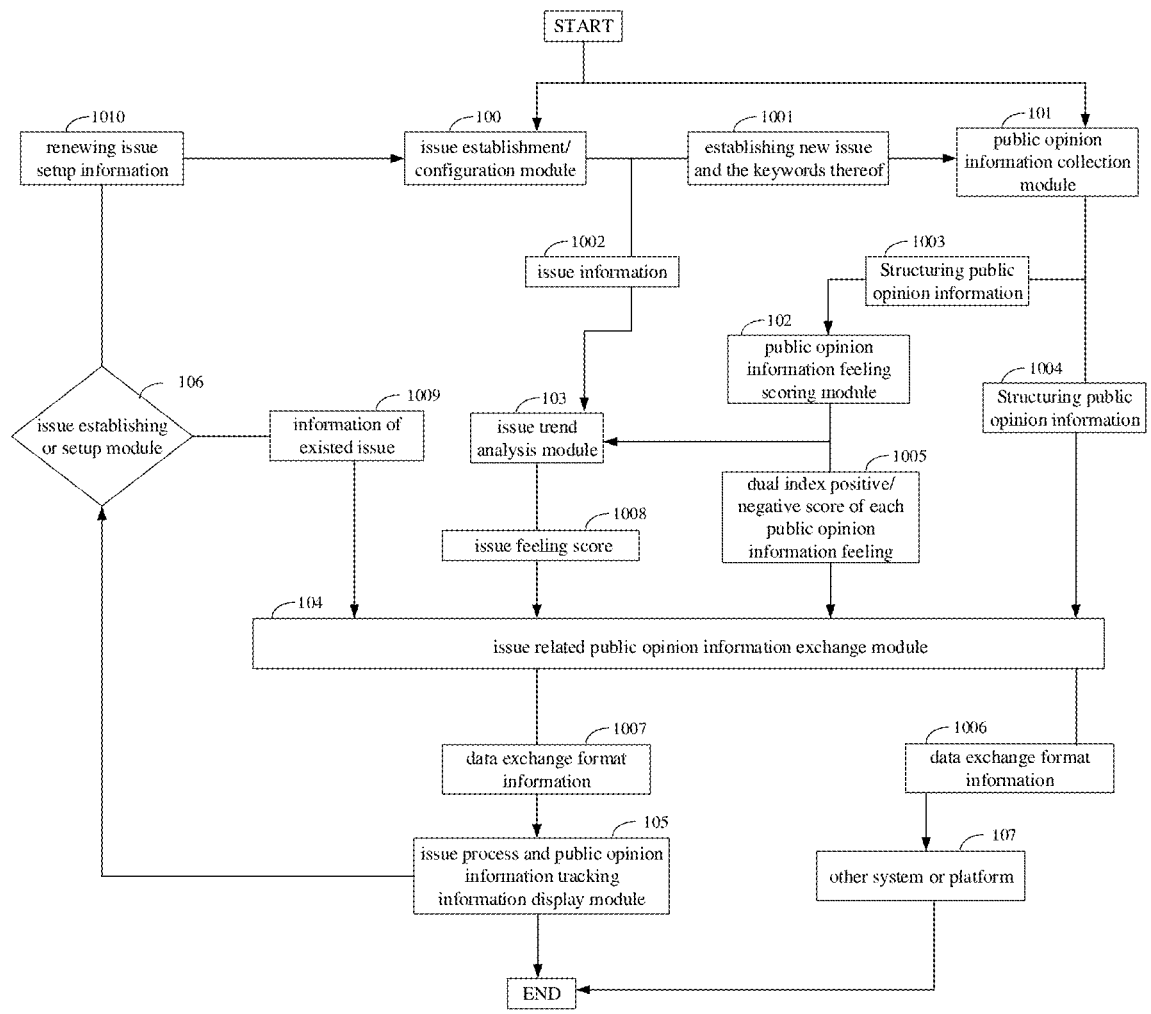
FIG. 1 shows a block diagram of issue-manage-style internet public opinion evaluation management system of the present invention.

FIG. 1 shows the main flow of the present invention. The flow of the present invention is based on issue management. After entering the system, issue setup information of the issue establishment/configuration module 100 is read first. If the issue establishment/configuration module 100 is empty, then operation of "establishing new issue and the keywords thereof" is executed by step 1001 of "establishing new issue and the keywords thereof" in system.

By step 1001 of "establishing new issue and the keywords thereof", it is able to access issue establishment/configuration module 100 to retrieve raw data for being transmitted into structured information for storage. Structured format comprises title, author, source, web-site, content, and etc. It is able to divide them into four types of: social web-site (such as FACEBOOK, Plurk, Twitter, and etc.), news media, interesting community (such as PTT, Mobile01, Baby Home, famous blog, and etc.), application software market of smart phone (such as Google Play, Apple iTunes, Windows Market, and etc.). Steps of "Structuring public opinion information" 1003 and 1004 are executed by the public opinion information feeling scoring module 102 and the method of the present invention for generating dual index positive/negative score of each public opinion information feeling in step 1005, which comprises positive/negative evaluation scores of text analysis, and positive/negative evaluation scores of community Fuzzy analysis.

Each public opinion information evaluation score retrieved in step 1005, such as text evaluation index positive/negative evaluation score, community Fuzzy evaluation index positive/negative evaluation score, or combined of the two indexes, by the public opinion information feeling scoring module 102 can be adopted by the issue trend analysis module 103 to derive issue reputation score focused on issues. The two indexes can be combined by conventional methods such as arithmetic mean, weighed mean, geometric mean, difference, quotient, sum, or product of the text evaluation and community Fuzzy evaluation.

Evaluation score of the public opinion information feeling scoring module 102 and issue trend analysis module 103 takes calendar day as calculation unit. Based on the daily evaluation, it applies conventional formula such as sum, arithmetic mean, mode, or median transformation to provide weekly evaluation, monthly evaluation, seasonal evaluation, or annual evaluation.

The information generated by the public opinion information collection module 101, public opinion information feeling scoring module 102, issue trend analysis module 103 and issue establishing or setup module 106 are integrated in issue related public opinion information exchange module 104. All issues information is provided outward through API in JSON (JavaScript Object Notation) data exchange language, XML (eXtensible Markup Language), DSML (Directory Services Markup Language), YAML (YAML Ain't Markup Language). The standard result is reported to the issue process and public opinion information tracking information display module 105 in step 1007 of "data exchange format information". Thus the issue can be handled and tracked. Also, the standard result can be reported to other system or platform 107 for other applications thereon in step 1006 of "data exchange format information".

After the issue process and public opinion information tracking information display module 105, people handle and operate issue management and tracking. The user can adjust issue information by issue establishing or setup module 106 after reading the information, and if the user selects to establish/setup issue, then step 1010 of "renewing issue setup information" is executed and the method goes back to operation of issue establishment/configuration module 100. If the user selects to not establish/setup issue, then the issue information would be integrated in issue related public opinion information exchange module 104, and step 1009 of "providing related information of all established/setup issues" is executed.

Figure 2:
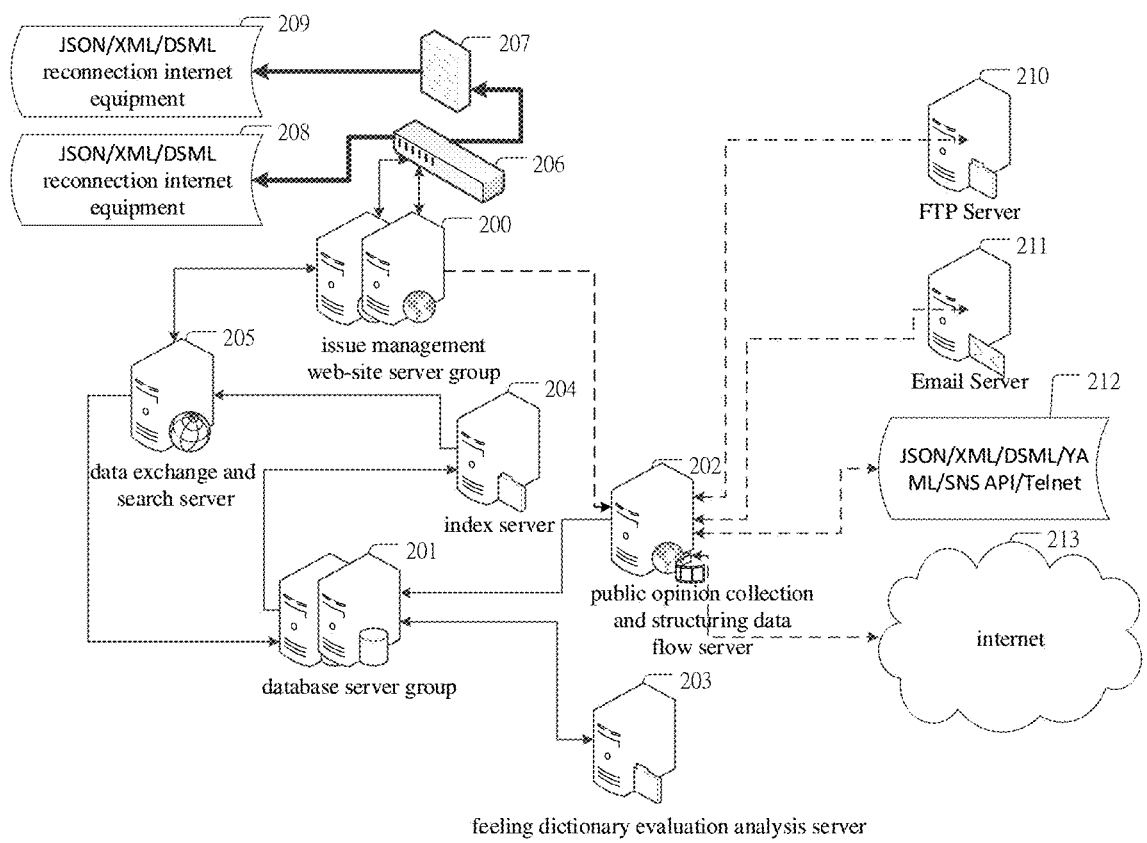
FIG. 2 shows a diagram of issue-manage-style internet public opinion evaluation management system of the present invention.

Refer to FIG. 2, after a plurality of Virtual Machines, VM, are independently setup, the issue management web-site server group 200 can establish/setup configurations corresponding to each issue and related keywords, and Web layer service and issue management API are also included. The issue management web-site server group 200 sends the keyword group to the public opinion information collection and structuring data flow public opinion information collection and structuring data flow server 202. The public opinion information collection and structuring data flow server 202 takes the keyword group as reference for retrieving under analysis raw data from internet 213 and temperately storing the data in public opinion information collection and structuring data flow public opinion information collection and structuring data flow server 202.

The public opinion information collection and structuring data flow server 202 comprises a plurality of information access and transforming modules, and it is able to periodically transform the temporally temperately stores the raw data retrieved from internet 213 into structured format comprising fixed format structured information such as title, author, content, publishing time, retrieving time, data transforming time, web-site address, web-site page tag, information sources, information source web-site category, reading count, response count. It is able to divide web-sites into four types of: social web-site (such as FACEBOOK, Plurk, Twitter, and etc.), news media, interesting community (such as PTT, Mobile01, Baby Home, famous blog, and etc.), application software market of smart phone (such as Google Play, Apple iTunes, Windows Market, and etc.).

Public opinion collection and structuring data flow server 202 retrieves public opinion information CSV or TXT files from FTP server 210 via FTP/SFTP protocol, and then analysis text file by separation signs for later structure transformation. The public opinion information collection and structuring data flow server 202 applies Java to pass security check and then gets Windows Office file (such as .docx or .xlsx) from the email server 211, and then retrieves public opinion information among the documents based on Office Open XML for later structure transformation.

Other documents, such as non-OFFICE document, fixed delimited text file, file unable to retrieve by dredge technology, the public opinion information collection and structuring data flow server 202 applies fixed format and API to exchange data and get public opinion information by JSON (JavaScript Object Notation) data exchange language, XML (eXtensible Markup Language), DSML (Directory Services Markup Language), YAML (YAML Ain't Markup Language). For hot social web-site, such as Facebook, Twitter, Plurk, or Google+, it can get published article, number of sharing, number of reply, number of "like" click, community tag by SNS API provided by each social web-site, it also can get embedded outside social web-site information (such as number of sharing, number of reply, number of "like" click, community tag of Facebook) of a web-site information (such as news web-site), and then structurally transform whatever they get from the web-site together. For hot BBS in Taiwan, it applies telnet standard to access assigned forum on BBS, imitates user reading mode by select article according to date sequence, then the public opinion information collection and structuring data flow server 202 retrieves information back for structural transformation. All heterogeneous data are transformed into structured information corresponding to issue and predetermined format by public opinion information collection and structuring data flow public opinion information collection and structuring data flow server 202.

Public opinion collection and structuring data flow server 202 stores quantity of structured information in database server group 201, and a structural data searching index file is established in the index server 204. The public opinion information collection and structuring data flow public opinion information collection and structuring data flow server 202, after each time of storing transformed information, recall the feeling dictionary evaluation analysis server 203 for evaluation analysis through database server group 201. There is a reputation evaluation dictionary stored in the feeling dictionary evaluation analysis feeling dictionary evaluation analysis server 203. The reputation evaluation dictionary comprises each word of reputation with corresponding positive reputation score and negative reputation score. Also, a reputation dual-index positive/negative evaluation analysis method module comprising text reputation index analysis and community Fuzzy community index analysis, and an issue evaluation analysis method module can be established. The feeling dictionary evaluation analysis server 203 retrieves each structured public opinion information from the database server group 201, and then divides the content of article into portions, compares each word/sentence with reputation evaluation dictionary.

Positive text analysis reputation index is retrieved by the formula $$Ov_+(i) = \frac{\sum_{i=1}^{n} Wr_+(i)}{\text{the length of } W}$$

calculating positive text reputation index score of each public opinion information. And negative text analysis reputation index is retrieved by the formula $$Ov_-(i) = \frac{\sum_{i=1}^{n} Wr_-(i)}{\text{the length of } W}$$

calculating negative text reputation index score of each public opinion information.

The feeling dictionary evaluation analysis server 203 gets number of "like" click, number of sharing, and number of reply of each structured public opinion information in social web-site from database server group 201, and then execute community Fuzzy community index analysis on each public opinion information by two formulas, wherein the formula $$u_{A+} = \begin{cases} 0, u < a_+ \\ \left(\frac{u - a_+}{b_+ - a_+}\right), a_+ \le u \le b_+ \\ 1, u > b_+ \end{cases}$$

is configured for calculating Fuzzy community positive reputation index of each public opinion information between 0 to 1, wherein the u equals to sum of number of "like" click and number of sharing (if the text is from FACEBOOK group or fans group, then the u equals to number of hits), wherein $a_+=20$, $b_+=200$ which are adjustable to enhance accuracy; the formula $$u_{A-} = \begin{cases} 0, \frac{k \times r}{u} < a_- \\ \left(\frac{\frac{k \times r}{u} - a_-}{b_- - a_-}\right), a_- \le \frac{k \times r}{u} \le b_{-1} \\ 1, \frac{k \times r}{u} > b_- \end{cases}$$

is configured for calculating Fuzzy community negative reputation index of each public opinion information, wherein the r equals to number of reply, and u equals to sum of number of "like" click and number of sharing (if the text is from FACEBOOK group or fans group, then the u equals to number of hits), wherein $k=100$, $a_-=2$, $b_-=10$, and if the number of reply is 10, and the sum of number of "like" click and number of sharing is 1000, then $$\frac{k \times r}{u} = 1, \frac{k \times r}{u} < 2,$$

and the Fuzzy community negative reputation index is zero representing low negative level. In another case, if the sum of number of "like" click and number of sharing is 1000, and the number of reply is larger than 100, then $$\frac{k \times r}{u} > 10,$$

which means the public opinion information Fuzzy negative reputation index is 1 representing high negative level, if the sum of number of "like" click and number of sharing is 1000, and the number of reply is between 20 to 100, then a negative index between 0 to 1 is derived. The user can adjust a_ and b_ to enhance accuracy.

The next embodiment shows applying the present invention on community issue analysis and issue tracking of user behavior of "like" click, sharing, reply, and other social tools, which may show higher accuracy of reference. After retrieving text reputation positive/negative index and community reputation positive/negative index, the present invention applies weighed mean of (120% community reputation index and 80% text reputation index)/2 to get positive evaluation value and negative evaluation value of each public opinion information. For example, if a community's reputations positive index of public opinion information is 0.5, and a text reputation positive index of the same public opinion information is 0.6, then the public opinion information positive index of the public opinion information is (120%×0.5+80%×0.6)/2=0.54, if a community reputation negative index of public opinion information is 0.15, and a text reputation negative index of the same public opinion information is 0.25, then the public opinion information negative index of the public opinion information is (120%× 0.15+80%×0.25)/2=0.19. After calculation of each public opinion information, the result shows positive/negative community reputation index, positive/negative text reputation index, positive/negative weighed mean of public opinion information evaluation value, and all the index and value would be stored in the database server group 201, also the index server 204 would establish an index searching file.

The feeling dictionary evaluation analysis server 203 would retrieve positive/negative evaluation of each public opinion information, and then check corresponding keyword information of each issue in the database server group 201. Thus, public opinion information of each issue in a certain time period can be understood. By calculating the public opinion information and corresponding evaluation with formula and different time period, it is able to get weekly evaluation, monthly evaluation, seasonal evaluation, or annual evaluation of an issue. Each evaluation of issue comprises positive and negative evaluations.

$$Iv(V) = \frac{\sum_{i=1}^{n} \frac{Vi}{\text{Log}_{base}(D_{now} - Di + C)}}{\text{Summary(Keywords)}} \quad \text{Formula}$$

is applied. By putting each public opinion information positive evaluation in Vi, time at 23:00 of a day, $D_{now}-Di=0$, base=10, C=10, if the issue comprises five keyword sets then Summary (Keywords)=5, and a daily positive evaluation of an issue is generated. Similarly, by putting each public opinion information negative evaluation in the formula, a daily negative evaluation of an issue is generated. For example, if the calculation is executed at 23:00 of a Saturday night, and $D_{now}-Di=7$, then a weekly evaluation is generated. If the calculation is executed at 23:00 by the end of a month, and $D_{now}-Di=$days of a month, then a monthly evaluation is generated. Similarly, it can get seasonal evaluation and annual evaluation. All issues, keywords, corresponding public opinion information, each evaluation of different time period are stored in the database server group 201, and the index server 204 establishes an index searching file.

The data exchange and search server 205 is configured with API for data exchange and search in response to outside demands. When a search is requested, it retrieves related information from the index server 204, and if it needs to be adjusted, it can add, modify, or delete data in the database server group 201. Then the database server group 201 would have the index server 204 establishing index again. The web-site of the system can be managed by issue management web-site server group 200, and the API of the data exchange and search server 205 can access the web-site to display requested information. Internal web-site or application programs are able to requested by the issue management web-site server group 200 via internet equipment 206 for calling data exchange and search data exchange and search server 205 to retrieve requested information. The information can be packaged by JSON/XML/DSML or other standard format. The outside web-site can access the system via firewall 207 to connect internet equipment 208, and then the issue management web-site server group 200 calls API of data exchange and search server 205 to provide requested information. The information can be packaged by JSON/XML/DSML or other standard format for data synchronization or exchange.

Issue management web-site server group 200 can establish issue, and the data exchange and search data exchange and search server 205 can manage each issue including modifying, deleting, adjusting keyword, recording issue handle method, reporting issue, email issues, tracking issues, search public opinion information related to the issue, alerting important issue, or alerting huge quantity of public opinion information.

Figure 3:
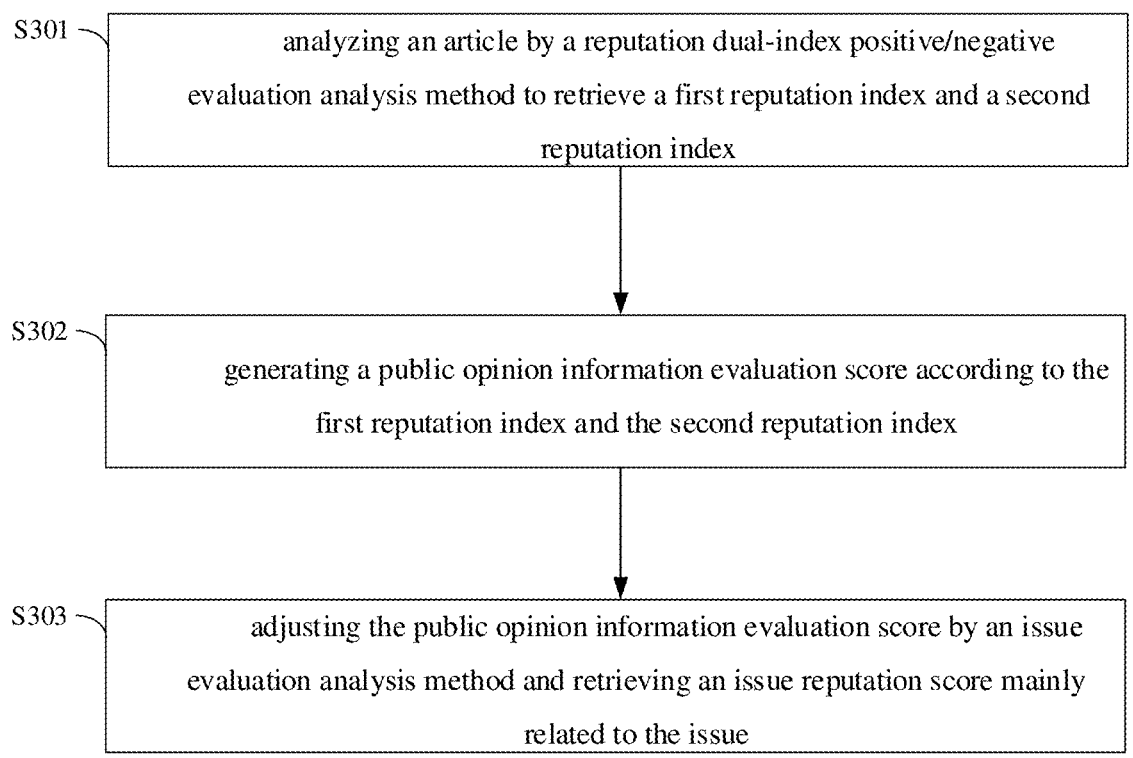
FIG. 3 shows a flow diagram of issue-manage-style internet public opinion evaluation management method of the present invention.

FIG. 3 shows method flow of the present invention of issue-manage-style internet public opinion information evaluation management method, which comprises steps of:

S301: analyzing an article by a reputation dual-index positive/negative evaluation analysis method to retrieve a first reputation index and a second reputation index;

S302: generating a public opinion information evaluation score according to the first reputation index and the second reputation index; and S303: adjusting the public opinion information evaluation score by an issue evaluation analysis method and retrieving an issue reputation score mainly related to the issue.

More particularly, issue evaluation analysis method uses evaluation Vi for further operation, and the evaluation Vi is retrieved after each public opinion information analysis. A Data_Function( ) is applied in public opinion information evaluation value Vi according to time period for calculation (such as a day, a week, or a month) at each calculation time. For example, if an evaluation of an issue corresponding to time period from 6/25 to 7/15 is generated on 7/1, it can say that each related public opinion information evaluation value happened on 7/1 is free from date influence, but the evaluation value happened from 6/25 to 6/30 is done for a while, that means the evaluation effect should be reduced. It can say that the evaluation on 6/25 only has half effective evaluation value, and then the evaluation value of public opinion information on 6/25 should be rendered as Vi/2. That is what Date_Function( ) means, it can adjust according to different public opinion information evaluation value on different date. Analysis formula presents as below:

$$Iv(V) = \frac{\sum_{i=1}^{n} \text{Date\_Function}(Vi)}{\text{Summary(Keywords)}}$$

After adjusting Vi by the aforementioned formula, the sum of a plurality of evaluation can be divided by a particular number representing a number of keyword groups assigned by the issue. Thus the influence of number of keyword groups can be reduced. For example, if an issue assigns 10 keyword groups for searching public opinion information, then the particular number is 10, and an issue evaluation value Iv(V) can be derived. Wherein, the method of retrieving public opinion information evaluation can be a reputation dual-index positive/negative evaluation analysis method or a reputation index selection method. For different industries, Date_Function( ) can be adjusted respectively, and the following description illustrates some methods.
log formula $$Iv(V) = \frac{\sum_{i=1}^{n} \frac{Vi}{\text{Log}_{base}(D_{now} - D_{aim} + C)}}{\text{Summary(Keywords)}}$$

The issue evaluation method is applied when an issue attracts many public opinion information, the method can focus on the issue for evaluation calculation. When each Vi does not need significant adjustment during a certain period, the time period can be a base of Log. Issue evaluation Iv (V) represents sum operation of event influence factors based on public opinion information evaluation score. N represents related number of public opinion information of an issue, for example if there 30 public opinion information related to an issue, then n=30. Ni represents public opinion information event influence factor of an issue during a certain time period, it can calculated based on day, and Vi value represents evaluation score of each public opinion information article on that day.

Vi, representing evaluation score of each article, is calculated by the reputation dual-index positive/negative evaluation analysis method and reputation index selection method. The reputation dual-index positive/negative evaluation analysis method and reputation index selection methods are illustrated, for example, as below. Wherein Vi represents score of each article, which can be text analysis reputation index positive/negative evaluation score, or community Fuzzy analysis reputation index positive/negative evaluation score, or any other meaningful score recognized by the industry that combines the two indexes.

Formula has to consider time influence, wherein $D_{now}$ represents assigned analysis date, $D_{aim}$ represents public opinion information happened date, $D_{now} - D_{aim}$ represents time difference between assigned analysis date and public opinion information happened date. For example, if an assigned date of an issue is today, and related public opinion information happened two days ago, then $D_{now} - D_{aim} = 2$. The formula takes a point of view that as time goes by, the influence of a particular public opinion information event factor would decrease, and the latest score should not be influenced by time. Thus, the formula takes Log operation based on time period as $\text{Log}(D_{now} - D_{aim})$. To ensure get Log value=1 when $D_{now} = D_{aim}$, evaluations taken on the same day are free from time influence, and prevent from Log 0 error, the formula takes a fixed parameter C for correction and accuracy, and is written as $\text{Log}_{base}(D_{now} - D_{aim} + C)$.

The Log base of $\text{Log}_{base}$ is designed for user's observation. For example, if a company renders that public opinion information is slightly influenced by time period within 10 days, the formula can take $\text{Log}_{10}$ for analysis, which means k=10 (meanwhile C=10). If a company renders that public opinion information is slightly influenced by time period within 2 days, but would be significantly decreased after 3 days, the formula can take $\text{Log}_2$ for analysis, which means k=2 (meanwhile C=2). Evaluation of an issue is derived by formula $$\sum_{i=1}^{n} \frac{Vi}{\text{Log}_{base}(D_{now} - D_{aim} + C)}$$

The result would be divided by number of keyword groups assigned by the issue to dilute influence of number of keyword groups. If the issue assigns 10 keyword groups for searching public opinion information, the number would be 10.
linear regression method (is this a heading? Please clarify)
Linear regression method takes formula as $$Iv(V) = \frac{a + b \sum_{i=1}^{n} Vi}{\text{Summary(Keywords)}}$$

The method takes regression in calculating evaluation of issue with influence parameters of past information that reduces as time goes by. Evaluation of issue Iv (V) and public opinion information evaluation Vi are dependent. If the industry shows that influence of public opinion information evaluation is tended to be linearly decreased as time goes by, then the linear regression method can be used. To retrieve Iv (V), the formula has to limit sampling range and sampling targets. The range can be a past date and a present date effective public opinion information data, that is Vi set of past date, and the sampling targets is limited on an issue with Summary(Keywords)=1. Iv value can be precisely determined by personal evaluation, which means that the Iv_person value is evaluated by present perspective. For example, if today is 7/1, and assigned calculation date is 6/23, the present Vi is 10, and the user wants to know the issue on 6/23 would present what IV value on 7/1? Now the method would be repeated m times until the date of today as time goes by, then it gets {Vi set1, Vi set 2, Vi set 3 . . . Vi set m}, and corresponding personal evaluating variables {Iv1, Iv2, Iv3 . . . Ivm}

By using concept of linear regression formula, b can be solved first. In the formula, "a" represents the intercept of the regression line and vertical axis, and "b" represents slope rate, i.e. variable of Vi corresponding to each time unit change. Then "a" can be retrieved by subtracting product of mean of sum Vi times "b" from mean of Iv. After "a" and "b" are retrieved, the formula can be calculated again by the "a" and "b" on the date to get issue evaluation.

Taking daily issue evaluation calculation as example, according to past reference data, if a=0.01 and b=0.9, then the formula presents $$Iv(V) = \frac{-0.01 + 0.9 \sum_{i=1}^{n} Vi}{\text{Summary(Keywords)}}.$$

If the user wants to know issue evaluation analysis on a particular date, as long as the issue is within the assigned date range, the formula can be applied to get Vi values of public opinion information corresponding to the issue, and the Iv (V) can be retrieved to calculate the past evaluations of the issue.

double declining balance method (is this a heading? Please clarify)

The issue evaluation analysis method applies conventional cost analysis method in accounting field, which is easier that regression method. The method is suitable for an reputation evaluation that is influenced by date by a ratio, and the influence can be ignored after a certain date period. The double declining balance formula is as below:

$$Iv(V) = \frac{[(1/Dm) \times P]^{\wedge(D_{now}-D_{aim})} \times \sum_{i=1}^{n} Vi}{\text{Summary(Keywords)}}.$$

The method takes double declining concept to retrieve issue evaluation Iv(V) of a particular date or time period. The user assigns a target date Dm and declining times based on his own demand or experience. For example, if an user does not want to consider an issue happened more than one month ago, and it declines every half day, then Dm=30 (day)×2=60. Further, a multiple P is needed. If the user assigned the multiple is 3, then p=3. $D_{now}$ represents assigned analysis date, $D_{aim}$ represents public opinion information happened date, and $D_{now}$-$D_{aim}$ represents time period defined by the assigned analysis date and the public opinion information happened date. If the assigned analysis date of an issue is today, and one public opinion information happened on two days ago, then $D_{now}$-$D_{aim}$=2, and the issue calculation formula is $$Iv(V) = \frac{[(1/60) \times 3]^{\wedge 2} \times \sum_{i=1}^{n} Vi}{\text{Summary(Keywords)}}.$$

By replacing Vi of each public opinion information of the issue happened on that date in the formula, issue evaluation Iv (V) can be retrieved.

Reputation dual-index positive/negative evaluation analysis method means a method that takes text analysis evaluation and community analysis evaluation of an article. One reputation index is text analysis reputation index, which takes database of a reputation evaluation dictionary as reference. Each reputation word has positive and negative scores. In an article, after slicing words thereof, it is able to know the quantity of words, i.e. (the length of W). If the word hits database of reputation evaluation dictionary, it can earn a word semantic positive evaluation $Wr_+$ and a word semantic negative evaluation $Wr_-$. Then a word weighed analysis method can be applied to calculate a positive reputation semantic index $Ov_+$ and a negative reputation semantic index $Ov_-$ of an article. The formula for calculating positive reputation semantic index $Ov_+$ is $$Ov_+(i) = \frac{\sum_{i=1}^{n} Wr_+(i)}{\text{the length of } W}.$$

The formula for calculating negative reputation semantic index $Ov_-$ is $$Ov_-(i) = \frac{\sum_{i=1}^{n} Wr_-(i)}{\text{the length of } W}.$$

Another reputation index is community Fuzzy analysis reputation index. Generally web-sites provide simple recognition tools such as "like", "Push", "sharing", "hits" for published article provided by the users. By using Fuzzy analysis method, it can assign a $a_+$ as low level of positive identity and a $b_+$ as high level of positive identity, and u represents sum of pro counts. If u does not reach $a_+$, then the community positive reputation index is 0, if u is greater than $b_+$, then the community positive reputation index is 1. And a formula can be used to determine Fuzzy community positive reputation index between 0 and 1.

Community negative reputation index includes reply counts of community article as an analysis parameter. It considers that if the reader would take "reply" function, which is more complex than convenient pro identify tools in community web-site, it may mean that the reader is against the community article. If the reply counts is close to the identify counts (such as "like", "Push", "sharing", "hits"), then it would be rendered as higher negative. The method considers reply counts as negative reputation to calculate community negative reputation semantic index by Fuzzy analysis method. It assigns a $a_-$ as low level of negative identity and a $b_-$ as high level of negative identity, u represents sum of pro counts, r represents sum of reply counts, and k is a constant for easy calculation. When r:u ratio does not reach $a_-$, the community negative reputation index is 0, when r:u ratio is larger than $b_-$, the community negative reputation index is 1.

$$m = \frac{k \times r}{u},$$

and if m is among $a_-$ and $b_-$, then a Fuzzy community negative reputation index between 0 and 1 is derived by the formula.

Formula for calculating Fuzzy community positive reputation index is as below:

$$u_{A+} = \begin{cases} 0, u < a_+ \\ \left(\frac{u - a_+}{b_+ - a_+}\right), a_+ \leq u \leq b_+ \\ 1, u > b_+ \end{cases}.$$

Formula for calculating Fuzzy community negative reputation index is as below:

$$u_{A-} = \begin{cases} 0, \frac{k \times r}{u} < a_- \\ \left(\frac{\frac{k \times r}{u} - a_-}{b_- - a_-}\right), a_- \leq m \leq b_- \\ 1, \frac{k \times r}{u} > b_- \end{cases}.$$

Reputation Index Selection Method

Each public opinion information evaluation score that derived from public opinion information reputation evaluation module (taking reputation dual-index positive/negative evaluation analysis method) can be applied in different applications, it can choose text evaluation index positive/negative evaluation score, or community Fuzzy evaluation index positive/negative evaluation score. Or the two indexes can be combined by conventional methods such as arithmetic mean, weighed mean, geometric mean, difference, quotient, sum, or product of the text evaluation and community Fuzzy evaluation. The public opinion information score can be replaced in issue evaluation analysis method to get issue reputation score of the issue.

As aforementioned, the issue-manage-style internet public opinion information evaluation management system and method thereof of the present invention can be applied in all industries, organizations, authorities, and personal concerned public opinion information data/information collection. Further, it can combine kinds of module of text collection/process, data standard exchange/transform, text evaluation analysis, community evaluation analysis, and issue management, thus the operation unit can handle user's evaluation and efficiently monitor latest message on internet community media to deliver fast response to keep good customer relationship and company reputation.

What is claimed is:

1. An issue-manage-style internet public opinion information evaluation management method, comprising steps of:
    configuring an issue management web-site server to establish/setup each issue and related keyword;
    configuring a public opinion information collection and structuring data flow server connecting with the issue management web-site server to receive the keyword and to collect an article in accordance with the keyword, wherein the article is collected from a plurality of heterogeneous data sources and transferred the data into a structured data format for storage by technologies of OFFICE Open XML, format text, international standard of data exchange, dredge technology, social network access interface, or Telnet record;
    configuring a database server connecting with the public opinion information collection and structuring data flow server connecting with the issue management web-site server to store the structured data format;
    configuring a feeling dictionary evaluation analysis server connecting with the database server to analyze an article in accordance with the structured data format and using a reputation dual-index positive/negative evaluation analysis method comprising a text reputation index analysis and a community Fuzzy community index analysis to retrieve a first reputation index and a second reputation index, wherein the feeling dictionary evaluation analysis server compares the structured data format with a reputation evaluation dictionary to produce a reputation score, and further uses the text reputation index analysis to calculate the reputation score to produce the first reputation index, and wherein the feeling dictionary evaluation analysis server uses the community Fuzzy community index analysis to analyze the structured data format to produce the second reputation index;
    generating, by the feeling dictionary evaluation analysis server, a public opinion information evaluation score according to the first reputation index and the second reputation index, wherein the public opinion information evaluation score is a mean or a weighted mean of the first reputation index and the second reputation index; and
    adjusting, by the feeling dictionary evaluation analysis server, the public opinion information evaluation score by an issue evaluation analysis method and retrieving an issue reputation score mainly related to the issue.

2. The method as claimed in claim 1, wherein the issue evaluation analysis method is configured to adjust the public opinion information evaluation score according to a time.

3. The method as claimed in claim 2, wherein the issue evaluation analysis method adjusts the public opinion information evaluation score according to a log formula, a double declining balance method, or a linear regression method.

4. The method as claimed in claim 1, wherein the reputation dual-index positive/negative evaluation analysis method is configured to retrieve the first reputation index and the second reputation index according to a text analysis method and a community analysis method.

5. The method as claimed in claim 1, wherein the first reputation index is a text analysis reputation index, and the second reputation index is a community fuzzy analysis reputation index.

6. An issue-manage-style internet public opinion information evaluation management method, comprising steps of:
    configuring an issue management web-site server to establish/setup each issue and related keyword;
    configuring a public opinion information collection and structuring data flow server connecting with the issue management web-site server to receive the keyword and to collect an article in accordance with the keyword, wherein the article is collected from a plurality of heterogeneous data sources and transferred the data into a structured data format for storage by technologies of OFFICE Open XML, format text, international standard of data exchange, dredge technology, social network access interface, or Telnet record;
    configuring a database server connecting with the public opinion information collection and structuring data flow server connecting with the issue management web-site server to store the structured data format;
    configuring an index server connecting with the database server to establishes an index searching file, and configuring a data exchange and search server connecting with the index server connecting and the database server to provide searching and data-changing;
    configuring a feeling dictionary evaluation analysis server connecting with the database server to analyze an article in accordance with the structured data format and using a reputation dual-index positive/negative evaluation analysis method comprising a text reputation index analysis and a community Fuzzy community index analysis to retrieve a first reputation index and a second reputation index, wherein the feeling dictionary evaluation analysis server compares the structured data format with a reputation evaluation dictionary to produce a reputation score, and further uses the text reputation index analysis to calculate the reputation score to produce the first reputation index, and wherein the feeling dictionary evaluation analysis server uses the community Fuzzy community index analysis to analyze the structured data format to produce the second reputation index;
    generating, by the feeling dictionary evaluation analysis server, a public opinion information evaluation score according to the first reputation index and the second reputation index, wherein the public opinion information evaluation score is a mean or a weighted mean of the first reputation index and the second reputation index; and adjusting, by the feeling dictionary evaluation analysis server, the public opinion information evaluation score by an issue evaluation analysis method and retrieving an issue reputation score mainly related to the issue.

* * * * *